United States Patent
Reed

(10) Patent No.: US 10,738,331 B2
(45) Date of Patent: Aug. 11, 2020

(54) BACTERIA BASED CELLULOSIC ETHANOL FERMENTATION PROCESS

(71) Applicant: Tavis Reed, Oswego, IL (US)

(72) Inventor: Tavis Reed, Oswego, IL (US)

(*) Notice: Subject to any disclaimer, the term of this patent is extended or adjusted under 35 U.S.C. 154(b) by 344 days.

(21) Appl. No.: 15/738,390

(22) PCT Filed: Jun. 7, 2016

(86) PCT No.: PCT/US2016/036195
§ 371 (c)(1),
(2) Date: Dec. 20, 2017

(87) PCT Pub. No.: WO2016/209612
PCT Pub. Date: Dec. 29, 2016

(65) Prior Publication Data
US 2019/0161773 A1   May 30, 2019

Related U.S. Application Data

(60) Provisional application No. 62/183,763, filed on Jun. 24, 2015.

(51) Int. Cl.
| | | |
|---|---|---|
| *C12P 7/14* | (2006.01) | |
| *C12P 7/06* | (2006.01) | |
| *C12P 7/20* | (2006.01) | |
| *C12P 7/54* | (2006.01) | |
| *C12P 7/56* | (2006.01) | |
| *C12P 7/10* | (2006.01) | |

(52) U.S. Cl.
CPC ............... *C12P 7/14* (2013.01); *C12P 7/065* (2013.01); *C12P 7/10* (2013.01); *C12P 7/20* (2013.01); *C12P 7/54* (2013.01); *C12P 7/56* (2013.01); *Y02E 50/16* (2013.01); *Y02E 50/17* (2013.01)

(58) Field of Classification Search
None
See application file for complete search history.

(56) References Cited

PUBLICATIONS

Srivastava, A. et al., J. Atoms Molec. 2012 vol. 2, pp. 214-222, reprinted by ProQuest pp. 1-6.*

* cited by examiner

*Primary Examiner* — Heidi Reese
(74) *Attorney, Agent, or Firm* — Mitchell Intellectual Property Law, PLLC

(57) ABSTRACT

A process for the creation of ethanol from cellulosic materials using the bacteria *Cellulomonas* sp. and aerobic *Zymomonas mobilis* in the same medium under the same conditions to breakdown cellulosic materials into glucose and to ferment that glucose into ethanol and three significant byproducts, glycerol, acetic acid, and lactic acid.

14 Claims, No Drawings

BACTERIA BASED CELLULOSIC ETHANOL FERMENTATION PROCESS

CLAIM OF PRIORITY

Priority is claimed to international PCT application Serial No. PCT/US2016/036195, filed Jun. 7, 2016, and to U.S. Provisional application Ser. No. 62/183,763, filed Jun. 24, 2015, which serves as the priority document for said PCT application.

BACKGROUND OF THE INVENTION

1. Field of the Invention

This invention relates to the field of ethanol production.

2. Description of the Related Art

The primary means used to produce ethanol involves the yeast fermentation of sugars or sugar containing products. The most common feedstock used in America for the creation of ethanol is corn. In the corn ethanol process, corn is treated until it is in a fermentable state. Once in this state, the corn is fermented by yeast into ethanol, and some byproducts.

Bacterial fermentation of sugars into ethanol has been experimented with. *Zymomonas mobilis* is a Gram negative, facultative anaerobic, non-sporulating, polarly-flagellated, rod-shaped bacterium which has been used to ferment sugars. See U.S. Pat. Nos. 4,403,034 and 4,443,544. It is the only species found in the genus *Zymomonas*. (LPSN entry for *Zymomonas*).

In recent years, more cellulosic ethanol processes have been developed. Most of the processes first use either chemicals or enzymes to break down the cellulose into sugars. They then ferment the sugars in a second step, using yeast. These processes are reported to require a significantly higher plant production investment as compared to ethanol production: $7/annual gallon production capacity vrs $1-3/annual gallon capacity. "*Feasibility Study for Co-Locating and Integrating Ethanol Production Plants from Corn Starch and Lignocellulosic Feedstocks*" (PDF). United States Department of Energy, January 2005; "*Determining the Cost of Producing Ethanol from Corn Starch and Lignocellulosic Feedstocks*" (PDF). U.S. Department of Agriculture and U.S. Department of Energy, October 2000.

*Zymomonas mobilis* bacteria has been used in the second stage of cellulosic ethanol production. However, its substrate range is limited to glucose, fructose and sucrose, which prevents the commercial usage of *Z. mobilis* It cannot ferment C5 sugars like xylose and arabinose which are important components of lignocellulosic hydrolysates. Unlike *E. coli* and yeast, *Z. mobilis* cannot tolerate toxic inhibitors present in lignocellulosic hydrolysates such as acetic acid and various phenolic compounds.[4] Concentration of acetic acid in lignocellulosic hydrolysates can be as high as 1.5% (w/v), which is well above the tolerance threshold of *Z. mobilis*. Doran-Peterson, Joy; Cook, Dana M.; Brandon, Sarah K. "Microbial conversion of sugars from plant biomass to lactic acid or ethanol". *The Plant Journal* 54(4): 582-592. doi: 10.1111/j.1365-313X.2008.03480.x.

It is reported that some species of bacteria have been found capable of direct conversion of a cellulose substrate into ethanol. One example is *Clostridium thermocellum*, which uses a complex cellulosome to break down cellulose and synthesize ethanol. However, *C. thermocellum* also produces other products during cellulose metabolism, including acetate and lactate, in addition to ethanol, lowering the efficiency of the process. Some research efforts are directed to optimizing ethanol production by genetically engineering bacteria that focus on the ethanol-producing pathway. https://en.wikipedia.org/wiki/Cellulosic_ethanol-cite_note-38 *University of Rochester Press Release*: Genome Sequencing Reveals Key to Viable Ethanol Production.

SUMMARY OF THE PRESENT INVENTION

The present invention comprises a one-step bacteria based process for the production of ethanol from cellulosic materials by fermenting cellulose in a fermentation medium containing both the bacteria *Cellulomonas* sp. and aerobic *Zymomonas mobilis*. The two bacteria work surprisingly well together in a common media and under common conditions, with *Cellulomonas* sp. breaking down cellulosic materials into glucose, and aerobic *Zymomonas mobilis*, fermenting that glucose into ethanol, glycerol, acetic acid, lactic acid, and several other byproducts.

DETAILED DESCRIPTION OF THE PREFERRED EMBODIMENTS

Cellulosic material, usually in the form of grass or weeds, is thoroughly cleaned to remove unwanted particles, like dirt, and is then sanitized to kill bacteria that could harm *Cellulomonas* sp. and aerobic *Zymomonas mobilis*. After this, the cellulosic material is added to a fermentation media comprising a mix of water and yeast extract. Once this media is created a small amount of *Cellulomonas* sp. And aerobic *Zymomonas mobilis* are added to the media. This process is capable of turning cellulose into ethanol because of the nature of the two bacteria *Cellulomonas* sp. and *Zymomonas mobilis*. *Cellulomonas* sp. produces the enzyme cellulase which breaks down cellulose, which is simply connected chains of glucose, into their glucose subunits. Aerobic *Zymomonas mobilis* then consumes some of the glucose produced and converts it into ethanol, glycerol, acetic add, lactic acid, as well several other financially insignificant byproducts. After approximately 24 hours *Zymomonas mobilis* begins to become inhibited by the ethanol it has produced. At this point fermentation is considered completed and the typical product and byproduct concentrations are as follows, 12%-14% ethanol, 4%-5% glycerol, 2%-3% acetic acid, and 1%-2% lactic add.

*Zymomonas mobilis* ZM4, ATCC Number is 31821, is the preferred strain of aerobic *Zymomonas mobilis*, and is believed to be the only aerobic *Zymomonas mobilis* available at the present time. The full name of this Strain on ATCC is: *Zymomonas mobilis* (Lindner) Kluyver and van Niel (ATCC® 31821™). The ATCC website indicates that it can be used to produce ethanol, specifically from molasses. The initial growth medium preferred for this strain as recommended by ATCC is:

| ATCC Medium: 1341 RM Medium | |
|---|---|
| Glucose | 20.0 g |
| Yeast Extract | 10.0 g |
| $K_2HPO_4$ | 2.0 g |
| Agar (if needed) | 15.0 g |
| DI water | 1,000 ml |
| Autoclave each component separately, combine, and adjust pH to 6.0. | |

Preparation of a small amount of aerobic *Zymomonas mobilis* for use in the fermentation medium is accomplished by placing a pellet of the bacteria containing about $10^8$ bacteria cells obtained from ATTC in 100 ml of the above initial growth media. After two weeks of growth in a shaking incubator at 30° C., 1 ml of the growth medium is removed and introduced into 50 ml of the fermentation medium. Scale up would involve using larger amounts of the above ingredients in similar proportions.

The preferred strain of *Cellulomonas* used is Strain [NCIB 11494], ATCC Number is 21399. It is an aerobic bacteria. The full name of this Strain on ATCC is: *Cellulomonas* sp. (ATCC® 21399™). It is known to degrade cellulose through the action of the cellulase which it produces. It is known for use in the production of food supplements for animals. The initial growth medium preferred for this strain as recommended by ATCC is:

ATCC Suggested Medium:

| ATCC medium: 464 *Cellulomonas* PTYG medium | |
|---|---|
| Peptone | 5.0 g |
| Tryptone (BD 211705) | 5.0 g |
| Yeast extract | 5.0 g |
| Glucose | 5.0 g |
| Agar | 15.0 g |
| Distilled water | 1,000 ml |
| Autoclave at 121° C. for 15 minutes. | |

Preparation of the *Cellulomonas* for use in the fermentation medium is accomplished in the same manner as above. A pellet of the *Cellulomonas* bacteria of the bacteria containing about $10^8$ bacteria cells obtained from ATTC is placed in 100 ml of the above initial growth media. After two weeks of growth in a shaking incubator at 30° C., 1 ml of the growth medium is removed and introduced into 50 ml of the fermentation medium. As above, scale up would involve using larger amounts of the above ingredients in similar proportions.

Any of a number of yeast extracts can be used. Yeast extract is die common name for various forms of processed yeast products made by extracting the cell contents (removing the cell walls); they are used as food additives or flavorings, or as nutrients for bacterial culture media. Autolyzed yeast extract consists of concentrations of yeast cells that are allowed to die and break up, so that the yeasts' endogenous digestive enzymes break their proteins down into simpler compounds (amino adds and peptides)

The preferred fermentation media is a mixture of yeast extract and water. Other nutrients, such as the peptone, tryptone and $K_2HPO_4$ used in the initial growth medium for the *Cellulomonas* and aerobic *Zymomonas mobilis* ZM4 bacteria can be added to the fermentation medium, but, surprisingly have been found unnecessary.

The weight ratio of cellulose to yeast extract in the fermentation media is from about 1:40 to about 2:1, with about 1:2 being preferred. Small amounts of *Cellulomonas* and Aerobic *Zymomonas* are used at about 1 ml of bacteria containing growth media as processed above per 25 to 50 ml of fermentation medium, preferably about 50 ml.

The medium preferably comprises a substantial excess of water, with respect to the quantity of cellulose to be processed. If the water content of the medium is too low, the ethanol concentration during fermentation will increase more rapidly, putting the bacteria to sleep and preventing further production from the cellulose present. Thus the efficiency of the process, in terms of ethanol yield per unit of cellulose, is reduced. On die other hand, increasing the concentration of cellulose in the fermentation medium seems to increase the rate at which ethanol is produced, such that higher concentrations can be achieved before the bacteria cease production. In the same period of time, e.g. 24 hours, a greater yield of ethanol per unit of water will be achieved if the amount of cellulose processed per unit of water is greater, than would be achieved if the amount of cellulose per unit of water were less. On the other hand, if die amount of cellulose per unit of water is less, the yield of ethanol per unit of cellulose will be greater. Thus there is a trade-off between efficiency of raw material usage and efficiency of time usage. Of course, additional cellulose would also have to be added as die original supply is converted.

The range for cellulose processed as a weight/volume percentage of water used seems to be from about 0.025% to about 1.0%, more preferably about 0.5%. The quantities of yeast extract, bacteria and optional nutrients such as peptone, tryptone and $K_2HPO_4$ used in the fermentation medium would be adjusted according to the quantity of cellulose to be processed per unit of water. The combined total of cellulose, yeast, bacteria and nutrients would thus typically comprise from about 0.05 to about 5%, more preferably about 1.0-2.0% weight/volume percent. Within this range, one can obtain a good yield of ethanol, glycerol, acetic and lactic acids, and maintain a good level of efficiency.

One can increase the yield per unit of cellulose processed, however, by producing in a continuous process. In a continuous process, one would draw off medium as ethanol is produced and dissolved into it, and replace it with fresh fermentation medium. Filters might be used to minimize the loss of bacteria as the water, ethanol and other soluble ingredients are drawn off. Thus for example the concentration of ethanol in the medium might be maintained at level of about 10% in the fermenter where the cellulose being processed is located, with fresh water and soluble nutrients being added as ethanol laden water is removed. Fresh cellulose would also be added as cellulose is consumed in the process.

A typical weight/volume percentage range of all ingredients in the fermentation medium, including the cellulose material, is as follows:

Cellulose: from about 0.025%-about 0.500%, preferably about 0.25%

Yeast extract: from about 0.25% to about 1.0%, preferably about 0.5%

*Cellulomonas*: a very small amount, about 1 ml of bacteria containing growth media as processed above per 50 ml of fermentation medium.

Aerobic *Zymomonas*: a very small amount, about 1 ml of bacteria containing growth media as processed above per 50 ml of fermentation medium.

Water: Q.S. to 100% volume

This would be true for a batch process medium, but also would be a desirable static state for the fermenter portion of a continuous process plant.

The fermentation is conducted at a temperature ranging from 30° C.-37° C. Surprisingly, the bacteria multiply very well together in this medium even without the peptone, tryptone and $K_2HPO_4$ used in the initial growth medium. However, such additional ingredients can optionally be used. Maximum fermentation typically takes approximately 24 hours.

This process can be utilized for either batch fermentation or continuous fermentation. Its most plentiful products are ethanol, acetic acid, glycerol, and lactic acid. The typical product and byproduct concentrations are as follows, 12%-14% ethanol, 4%-5% glycerol, 2%-3°/e acetic acid, and 1%-2% lactic acid.

EXPERIMENTAL DATA

Experiments were conducted based on various combinations of nutrients for the fermentation medium, and on processing different quantities of cellulose. The amounts indicated in table 1 below were placed in 50 ml water. Both bacteria were present in the medium in the amounts of about 1 ml of bacteria containing growth media as processed above per 50 ml of fermentation medium. Yeast extract was used in all of the examples. The flasks containing the cellulose and fermentation media were placed shaking incubator for 24 hours at 30° C.

TABLE 1

| Flask # | east Extract (g) | Peptone (g) | cryptone (g) | GHPO$_4$ (g) | cotton (g) | DI water c(ml) |
|---|---|---|---|---|---|---|
| 1 | 0.25 | 0.25 | 0.25 | 0 | 0.25 | 50 |
| 2 | 0.25 | 0 | 0 | 0.25 | 0.25 | 50 |
| 3 | 0.25 | 0.25 | 0.25 | 0.25 | 0.125 | 50 |
| 4 | 0.25 | 0.25 | 0.25 | 0.25 | 0.0625 | 50 |
| 5 | 0.25 | 0.25 | 0.25 | 0.25 | 0.03125 | 50 |

The results of the experiments are reflected in Table 2 below. The glucose content was calculated based on the amount of cellulose (cotton) present in the flask. The glucose consumed was determined as a function of the quantity of the ethanol, acetic acid, lactic acid and glycerol obtained. These product yield percentages were determined by Fourier Transform Infrared Spectroscopy (FTIR), measured against standard concentration graphs prepared for each of the ingredients.

| Flask # | Glucose in flask | Glucose Consumed by Z. mobilis | Ethanol % | Acetic acid % | Lactic acid % | Glycerol % |
|---|---|---|---|---|---|---|
| 1 | $1.39*10^{-3}$ moles | 17.86% | 22.13% | 1.81% | 1.56% | 4.03% |
| 2 | $1.39*10^{-3}$ moles | 19.45% | 24.10% | 3.03% | 5.51% | 1.10% |
| 3 | $6.93*10^{-4}$ moles | 23.08% | 14.26% | 3.71% | 1.39% | 4.03% |
| 4 | $3.47*10^{-4}$ moles | 45.80% | 14.17% | 1.51% | 1.80% | 5.50% |
| 5 | $1.73*10^{-4}$ moles | 88.76% | 13.69% | 3.81% | 1.39% | 4.75% |

As can be seen, the efficiency of the process per unit of cellulose increased as the weight/volume percentage cellulose relative to water decreased from 0.5% to 0.0625%. However the efficiency of the process per unit of time (24 hours in all examples) increased with the increase from 0.0625% to 0.5%.

The ethanol, glycerol, acetic acid, lactic acid and other products produced can be separated from the fermentation media by various known techniques. Fractional distillation, freeze separation, and gas or liquid phase molecular sieve dehydration are examples of such techniques which can be used.

Of course it is understood that the forgoing describes preferred embodiments of die invention and that various changes and alterations can be made without departing from the scope of the invention as set forth in die attached claims.

The invention claimed is:

1. A process for the production of ethanol and other fermentation products from cellulosic materials comprising: fermenting cellulose in a fermentation medium containing both the bacteria *Cellulomonas* sp. and aerobic *Zymomonas mobilis* in which the fermentation medium is water based, and the range for cellulose processed as a weight/volume percentage of water used is from about 0.025% to about 1.0%.

2. The process of claim 1 in which the weight/volume percentage of cellulose in water is about 0.5%.

3. The process of claim 1 in which the fermentation media includes yeast extract.

4. The process of claim 3 in which the weight ratio of cellulose to yeast extract in the fermentation media is from about 1:40 to about 2:1.

5. The process of claim 4 in which the weight ratio of cellulose to yeast extract in the fermentation media is about 1:2.

6. The process of claim 4 in which *Cellulomonas* and aerobic *Zymomonas* are initially introduced into the fermentation medium at about 1 ml of bacteria containing growth media per 25 to 50 ml of fermentation medium.

7. The process of claim 4 which is made continuous by drawing off fermentation medium as ethanol is produced and dissolved into it, and replacing it with fresh fermentation medium and cellulose to be processed.

8. The process of claim 7 in which filters are used to minimize the loss of bacteria as water, ethanol and other soluble ingredients are drawn off, such that the need for fresh addition of bacteria is minimized.

9. The process of claim 8 in which the concentration of ethanol in the medium is maintained at level of about 10% in the fermenter where the cellulose being processed is located, with fresh water, soluble nutrients and additional cellulose being added as ethanol laden water is removed.

10. The process of claim 1 which is made continuous by drawing off fermentation medium as ethanol is produced and dissolved into it, and replacing it with fresh fermentation medium and cellulose to be processed.

11. The process of claim 10 in which filters are used to minimize the loss of bacteria as water, ethanol and other soluble ingredients are drawn off, such that the need for fresh addition of bacteria is minimized.

12. The process of claim 11 in which the concentration of ethanol in the medium is maintained at level of about 10% in the fermenter where the cellulose being processed is located, with fresh water, soluble nutrients and additional cellulose being added as ethanol laden water is removed.

13. A process for the production of ethanol and other fermentation products from cellulosic materials comprising: fermenting cellulose in water based fermentation medium containing yeast extract and both the bacteria *Cellulomonas* sp. and aerobic *Zymomonas* mobile, where the amount of cellulose processed as a weight/volume percentage of water used is about 0.5%, and the weight ratio of cellulose to yeast extract in the fermentation media is about 1:2.

14. The process of claim 13 in which *Cellulomonas* and aerobic *Zymomonas* are initially introduced into the fermentation medium at about 1 ml of bacteria containing growth media per 25 to 50 ml of fermentation medium.

\* \* \* \* \*